United States Patent [19]

Sarofeen et al.

[11] Patent Number: 4,546,379
[45] Date of Patent: Oct. 8, 1985

[54] INDEPENDENT COLOR ADJUSTMENT FOR A VIDEO SYSTEM

[75] Inventors: Joseph J. Sarofeen, Auburn, N.Y.; David M. Fischer, Waltham, Mass.

[73] Assignee: Welch Allyn, Inc., Skaneateles Falls, N.Y.

[21] Appl. No.: 487,070

[22] Filed: Apr. 21, 1983

[51] Int. Cl.[4] .............................................. H04N 9/04
[52] U.S. Cl. ........................................ 358/42; 358/98
[58] Field of Search ................ 358/41, 42, 98; 128/6, 128/11, 13, 18

[56] References Cited

U.S. PATENT DOCUMENTS

Re. 31,289  6/1983  Moore et al. .......................... 358/98
Re. 31,290  6/1983  Moore et al. .......................... 358/98
4,253,447   3/1981  Moore et al. .......................... 358/98

Primary Examiner—Michael A. Masinick
Attorney, Agent, or Firm—Bruns and Wall

[57] ABSTRACT

Apparatus for use in sequential color imagery wherein three successive monochrome images are acquired by a video system and then displayed simultaneously upon a screen as a color picture. A flash lamp is used to sequentially illuminate a target through a color wheel and thus create three primary color separated images which are recorded in series by the video camera. The intensity of each image is controlled by varying the output of the lamp during each imaging sequence to balance the primary colors used to recreate an original target upon the television screen so that the video picture accurately duplicates the colors found in the original.

7 Claims, 1 Drawing Figure

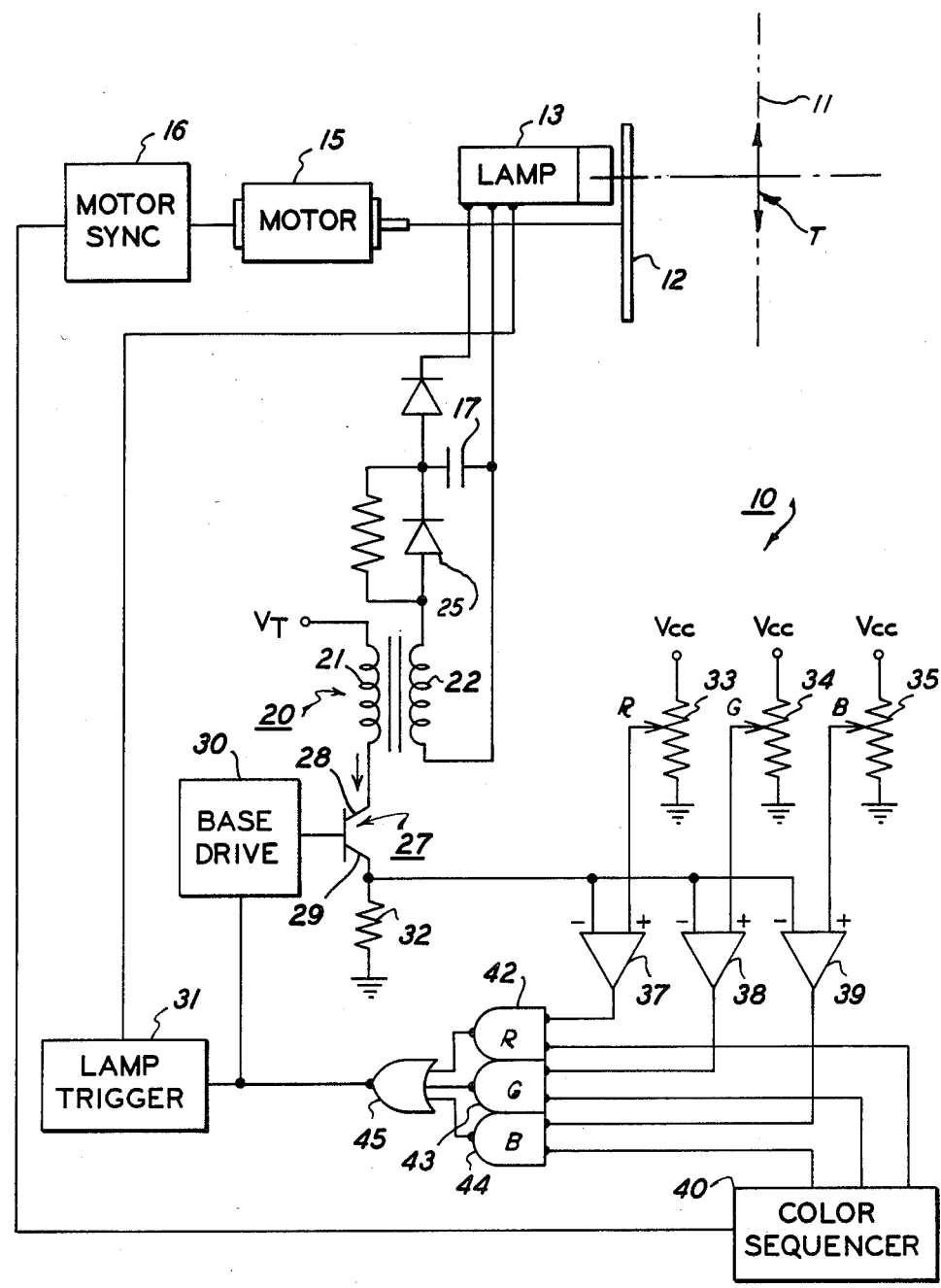

INDEPENDENT COLOR ADJUSTMENT FOR A VIDEO SYSTEM

BACKGROUND OF THE INVENTION

The invention relates to sequential color imagery and, in particular, to balancing colors in a video system using sequential color imagery.

With the advent of small charge coupled devices (CCD), it is now possible to construct an extremely small video camera that can be brought into confined areas that have heretofore been found inaccessible by this type of video equipment. Typically, the camera will contain only a single black and white CCD image recorder. In order to generate a color picture, three color separated monochrome images of a traget are created and recorded during each video frame to derive information concerning the primaries of red, green and blue. An endoscope employing a small CCD equipped camera for viewing remote body cavities is disclosed by Kakinuma et al in U.S. Pat. No. 4,074,306. The Kakinuma et al instrument utilizes a color wheel to provide the necessary color separation. Red, green and blue filters are rotated past a lamp that is adapted to illuminate a target in the image plane of the camera. The color separated images are recorded in sequence by the camera and, after the signals are processed, the color images are laid down one over the other upon a Braun tube.

Beyond the disadvantages relating to sequentially laying down the color images on a Braun tube, the Kakinuma et al. system makes no provision for properly balancing the amount of color contained in each separated image so that when the images are recombined, the video picture accurately depicts the colors found in the original. As a consequence, the Kakinuma et al endoscope cannot deliver the color purity needed to make an accurate visual diagnosis of the viewed body region and the usefulness of the instrument is severely limited.

SUMMARY OF THE INVENTION

An object of this invention is to improve sequential color imagery used in video systems.

A further object of the present invention is to provide color balancing in a video imaging system utilizing a color wheel and a single light source to create color separated images of an original target.

Another object of the present invention is to automatically vary the intensity of a single lamp used to generate successive monochrome images in a video system so that the colors found in the readout picture accurately reflect the colors contained in the original target.

Yet another object of the present invention is to improve color endoscopes of the type utilizing sequential color imagery.

These and other objects of the present invention are attained by means of a flash lamp that is arranged to illuminate a target in the image plane of a video camera through a rotatable color wheel whereby the target is illuminated sequentially with red, green and blue light. The wheel is turned at a speed related to video speed so that a red, a green and a blue image are acquired during each video field. The voltage applied to the charge capacitor of the lamp is controlled during each imaging period to balance the intensity of the three color images so that the video picture accurately depicts the colors found in the original.

The charge capacitor is connected to the collector of a darlington transistor through means of a flyback transformer so that the charge voltage applied to the capacitor is limited by the amount of current flowing through the primary windings of the transformer. A resistor is placed in the emitter circuit of the transistor which senses the collector current and provides a voltage signal indicative thereof. The sensed voltage signal is simultaneously applied to an input on each of three separate comparators that are adapted to control the base drive of the transistor. An adjustable potentiometer is connected to the other input of each comparator. When the sensed voltage over the resistor reaches the preset potentiometer voltage, the output of the comparator goes to zero. A gating network is employed to connect each comparator to the base drive of the transistor in a sequence that is matched with the color sequencing of the video system whereby each potentiometer controls the transistor on time during a selected one of the video color fields. This, in turn, controls the amount of target illumination provided during each color imaging period so that the primary colors can be balanced to produce the desired color purity.

BRIEF DESCRIPTION OF THE DRAWINGS

For a better understanding of the invention and further features thereof, reference is had to the following detailed description of the invention which is to be read in conjunction with the accompanying drawing which diagrammatically illustrates a color wheel illumination system used to sequentially illuminate a target with light of different primary colors to create color separated target images for use in a video system.

DESCRIPTION OF THE INVENTION

A video system is disclosed in U.S. Pat. No. 4,253,447 to Moore et al. which relates to an improved color endoscope wherein three successive monochrome color separated images are acquired by a CCD equipped video camera. After processing, the images are displayed simultaneously on a video screen to create a full color picture of the target. Moore et al. uses three independent light sources to illuminate the target with red, green and blue light. The sources are activated in a timed sequence with the video system whereby image data relating to the three color images is acquired in a prescribed order during each video field. The present invention is intended to replace the three lamp configuration of Moore et al. with a color wheel that requires the use of a single flash lamp to both generate the required color separated images and to balance the primary colors to obtain color fidelity in the video picture.

With reference to the drawing there is shown an illumination system, generally referenced 10, that is intended for use in the endoscopic instrument disclosed by Moore et al. in the above noted patent, the disclosure of which is herein incorporated by reference to the extent necessary to understand the operation of the present invention. A target T at 11 is shown positioned in the image plane of a video camera (not shown) and the target is illuminated by a flash lamp 13 that is adapted to fire through a color wheel 12. A series of red, green and blue filters are mounted upon the wheel. The filters are moved in sequence through the light path of the lamp as the wheel turns. The wheel is coupled directly via shaft 14 to a synchronous motor 15. The speed of the wheel is regulated through the motor synchronization circuit 16 so that each of the three noted filters are passed through the light path during each video field. A color sequencer 40 is employed to coordinate the activity of the wheel so that red separated images are acquired during the red portion of the field and the green and blue images during the green and blue portion of the same field. The time duration of the red, green and blue imaging periods are substantially equal with a small time delay between each to allow the acquired data to be processed in the video system.

The light source 13 herein utilized is a conventional flash lamp which is sometimes referred to as an arc discharge lamp. As is well known in the art, the lamp includes a quartz envelope filled with an inert gas such as xenon or the like. A high voltage trigger pulse from the lamp trigger circuit 31 is applied to lamp electrodes to ionize the fill gas and thus provide a current path between the electrodes. Once triggered, a charge capacitor 17 contained in the lamp's discharge circuit is allowed to discharge through the electrodes thereby producing a high intensity flash of illumination. The intensity of the light emitted by the lamp during each flash period is related to the amount of voltage stored on the charge capacitor. The intensity may be expressed by the relationship:

$$E = \tfrac{1}{2} C V^2 \qquad (1)$$

where:
C is the capacitance of the capacitor, and
V is the stored voltage on the capacitor.

One side of charge capacitor 17 is connected to the secondary windings 22 of a flyback transformer 20 by means of a blocking diode 25. The primary windings 21 of the transformer in turn are connected in series between the collector of a darlington transistor 27 and voltage source $V_T$. A sensing resistor 32 is placed between the emitter 29 of the transistor and ground. The voltage dropped across the resistor is directly proportional to the collector current.

The base drive 30 of the transistor is controlled by means of three separate comparators 37–39 that are connected to the drive through a gating network. As shown in the drawing, the voltage dropped over resistor 32, which will herein be referred to as the sensed voltage, is applied to the negative input terminal of each of the three comparators. The second or positive input terminal of each comparator is connected to an independent voltage supply $V_{cc}$ through an adjustable potentiometer. Comparator 37 and potentiometer 33 form a red control circuit while comparator 38 and potentiometer 34 form a green control circuit and comparator 39 and potentiometer 35 form a blue control circuit. Each comparator is adapted to provide a zero output when the sensed voltage applied to the negative terminal reaches the value of the preset control voltage applied to the positive terminal.

The output of each comparator is applied to one of the three AND gates found in the gating network. The gates are enabled in a timed sequence by means of an enabling signal provided by the video sequencer 40. The red gate 42 is enabled during the red portion of each video field while the green gate 43 and blue gate 44 are similarly enabled during the green and blue portions of the field. The output from each AND gate is fed to an OR gate 45 and then on to both the trigger control circuit 31 and the base drive circuit 30 of the transistor. The drive circuit is arranged to turn on the transistor when a digital one is received from the gating network and likewise turn the transistor off when a digital zero is received.

OPERATION

At the beginning of a red video field, the red video gate 42 is enabled by the color sequencer 40 whereupon the output signal from the red comparator 37 is applied to the base drive 30 of the darlington transistor 27. The initial signal from the base drive turns on the transistor thus permitting current to flow through the primary windings of the flyback transformer 20. This current flow through the primary of the transformer builds up a field of energy in the transformer. When the current flow is ceased, the field collapses, inducing a voltage on the secondary which, in turn, forward biases diode 25 and charges capacitor 17. The voltage on the capacitor is directly related to the current that has passed through the primary windings and is expressed by the following relationship:

$$\tfrac{1}{2} C V^2 = \tfrac{1}{2}(L_p \times I^2_p) \qquad (2)$$

where:
$L_p$ is the inductance of the primary windings
$I_p$ is the current through the primary windings
The sensed voltage dropped over the resistor 32 is directly proportional to the collector current.

When the voltage over the resistor 32 reaches the value set into the red control potentiometer, the output of the red comparator goes to zero thus shutting off the transistor. This limits the amount of charge stored on the lamp charge capacitor in response to the red potentiometer setting. Once the capacitor has been charged, the lamp is triggered through the trigger circuit thus ionizing the fill gas and permitting the capacitor to discharge through the lamp. As noted above, the intensity of the light emitted by the lamp during the red flash period is directly related to the voltage on the charge capacitor and is thus controlled by the setting of the red potentiometer.

The intensity of the light utilized during the remaining primary color fields is similarly adjusted. Using the three potentiometer controls, the three primary colors presented in the video picture can be finely adjusted to balance the primaries to a point where the colors contained in the video picture accurately reflects the colors found in the target. The intensity of each primary color can furthermore be set and reset as required to furnish accurate target information any time the video is in operation. By use of the flyback transformer in the collector circuit of the darlington transistor, the lamp can be continually strobed at high rates during each color field without danger of the arc holding over between flashes. Power furnished to the lamp is dependent upon the amount of current passed through the primary windings of the flyback transformer and not transformer voltage. Accordingly, variations in applied voltage will not affect the intensity of the lamp and a more dependable picture is produced.

While this invention has been described with reference to the structure disclosed herein, it is not confined to the details set forth and this application is intended to cover any modifications or changes as may come within the scope of the following claims.

We claim:

1. In a video system wherein a target is imaged during each video field by illuminating the target sequentially with light of different primary colors, apparatus for adjusting the intensity of light used to illuminate the target for each primary color that includes a flash lamp having means for ionizing a fill gas contained in the lamp and a capacitor for discharging through the ionized gas to produce a flash whose intensity is proportional to the charge on the capacitor, a color wheel for passing a series of primary color filters between the lamp and target whereby the target is illuminated once with light of each primary color, a flyback transformer having a primary winding connected between a voltage source and the collector of a transistor and a secondary winding connected to the lamp capacitor for charging the capacitor when the transformer is deenergized, a sensing resistor connected between the emitter of the transistor and ground whereby voltage dropped over the resistor is proportional to the current flow through the primary winding of the transformer, a plurality of comparators that are equal in number to the number of primary colors, each comparator having a first input terminal connected over the sensing resistor and a second input terminal connected to a potentiometer, each of said comparators being arranged to provide a zero output signal when the sensed voltage equals the potentiometer voltage, gating means for applying the output signal of each comparator to the base of the transistor to turn the transistor off when the gated signal goes to zero, a control means for enabling the gating means in a timed sequence with each video field whereby the intensity of the lamp is controlled during each imaging cycle and a lamp trigger means for ionizing the lamp gas each time the transistor is shut off.

2. The apparatus of claim 1 that wherein the lamp trigger means is connected to the gating means.

3. The apparatus of claim 1 wherein the color wheel contains a red, a green and a blue filter and further includes three comparators that are arranged to control the intensity of the lamp during the red, green and blue imaging periods.

4. In a video system wherein a target is illuminated sequentially with light of different primary colors during each video field, apparatus for controlling the intensity of the light during each illumination sequence that includes a gas lamp having a fill gas, means to ionize the gas and a capacitor for discharging through the ionized gas to produce illumination that is proportional to the charge on said capacitor, means for changing the color output of the lamp during each illumination sequence, a flyback transformer coupled to the capacitor for charging the capacitor when the transformer field collapses, a transistor for connecting one winding of the transformer to ground whereby the transformer field collapses when the transistor is shut off, a resistor means for sensing the current flow through the transformer, a plurality of comparators equal in number to the number of illumination sequences in each video field, each comparator arranged to compare the voltage dropped over the resistor with a preset voltage and produce an output signal when the compared voltages are equal, gating means for applying the output of each comparator to the transistor to turn the transistor off upon receipt of a comparator output signal, enabling means associated with the gating means for applying the output of each comparator to the transistor in a sequence related to the illuminating sequence, and means to apply a trigger signal to the lamp to ionize the gas each time the transistor is shut off.

5. The apparatus of claim 4 that further includes means to adjust the preset voltage applied to each comparator.

6. The apparatus of claim 4 wherein the enabling means is a color sequencer in the video system.

7. The apparatus of claim 4 that further includes a blocking diode positioned between the transformer and the capacitor for preventing the capacitor from discharging through the transformer.

* * * * *